United States Patent [19]

Gotlieb et al.

[11] Patent Number: 5,405,449
[45] Date of Patent: Apr. 11, 1995

[54] PROCESS FOR PREPARING CHAIN-EXTENDED STARCH

[75] Inventors: Kornelis F. Gotlieb, Veendam; Peter M. Bruinenberg, Hoogezand; Johannes B. Schotting; Doede J. Binnema, both of Groningen, all of Netherlands

[73] Assignee: Cooperative Verkoop-en Productievereniging van Aardappelmeel en Derivaten AVEBE B.A.

[21] Appl. No.: 130,751

[22] Filed: Oct. 4, 1993

[30] Foreign Application Priority Data

Oct. 2, 1992 [NL] Netherlands ............... 9201711

[51] Int. Cl.6 ............................................. C08B 30/00
[52] U.S. Cl. ........................................ 127/71; 106/210; 106/213; 106/214; 536/41; 536/186; 536/102; 536/124; 536/126
[58] Field of Search ............... 106/210, 211, 212, 213, 106/214; 536/4.1, 102, 18.6, 124, 126; 127/71

[56] References Cited

U.S. PATENT DOCUMENTS

| | | | |
|---|---|---|---|
| 4,739,043 | 4/1988 | Defaye et al. | 536/18.6 |
| 4,766,207 | 8/1988 | Deger et al. | 536/18.6 |
| 4,847,372 | 7/1989 | Franz et al. | 536/127 |
| 4,859,590 | 8/1989 | Thiem et al. | 435/97 |
| 4,871,840 | 10/1989 | Kobayashi et al. | 536/103 |

OTHER PUBLICATIONS

Biochemical and Biophysical Research Communications, vol. 111, No. 2, 1983, pp. 530–536 [No Month].

*Primary Examiner*—Anthony Green
*Attorney, Agent, or Firm*—Hoffmann & Baron

[57] ABSTRACT

According to the invention, chain-extended starch is prepared in that starch is polymerized in an aqueous solution at pH 6.0–8.3 by means of glucosyl fluoride in the presence of inorganic phosphate, sucrose phosphorylase and potato phosphorylase.

4 Claims, No Drawings

PROCESS FOR PREPARING CHAIN-EXTENDED STARCH

The invention relates to a new enzymatic process for preparing chain-extended starch by means of the compound α-D-glucopyranosyl fluoride (also referred to in short as α-D-glucose-1-fluoride, G-1-F or glucosyl fluoride).

Usually, starch consists of two types of glucose polymers, viz. a strongly branched polymer (amylopectin) and a slightly branched polymer (amylose). The length of the outer chains of these starch molecules partly determines the rheological behavior of starch solutions. By extending the outer chains, starch products are obtained with a molecular structure deviating from the structure of the starting material. The chain-extended starch products can advantageously be used in specific applications.

It is known that under the influence of the enzyme potato phosphorylase (PP), maltopentaose can be formed from glucosyl fluoride and maltotetraose by chain-extension (D. Palm et al; Biochemical and Biophysical Research Communications, Vol. 111, No. 2, 1983, Mar. 16, pages 530–536). However, in an analogous process wherein dissolved starch is used instead of maltotetraose, in the presence of PP and G-1-F no chain extension by polymerization takes place (see Example 1). If instead of glucosyl fluoride, the compound α-D-glucose-1-phosphate (G-1-P) is used, starch chain extension does take place (see Example 2). While G-1-P is suitable for the preparation of chain-extended starch, G-1-F does not seem suitable according to the prior art for extension of the starch chains.

Applicant has now found that it is nevertheless possible to prepare chain-extended starch products by means of glucosyl fluoride, if in the reagent at pH 6.0 –8.3 in addition to potato phosphorylase, the enzyme sucrose phosphorylase (SP; also referred to as saccharose phosphorylase) and inorganic phosphate are present. The invention therefore relates to the preparation of chain-extended starch, wherein starch is polymerized in an aqueous solution at pH 6.0 –8.3 by means of glucosyl fluoride in the presence of inorganic phosphate, sucrose phosphorylase and potato phosphorylase.

In their totality, the reactions occurring in the reaction mixture can be summarized as follows:

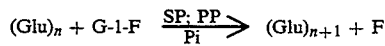

wherein,
(Glu)$_n$ = starch molecule
G-1-F = glucosyl fluoride
SP = sucrose phosphorylase
PP = potato phosphorylase
Pi = inorganic phosphate
(Glu)$_{n+1}$ = chain-extended starch molecule
F = fluoride As a result of this reaction, the chains of the starch molecules are extended by bonding of glucose units to the non-reducing ends. Particularly, by extension of the rather short outer chains of the amylopectin molecules, the amylose character of the starch products treated will be enhanced. This may be accompanied by changes of the rheological properties, of the starch solutions, such as viscosity and gelling behavior. Hence, the invention offers the possibility of preparing a new class of starch derivatives an enzymatic route.

As starting material for the process according to the invention starch is used. The term starch here refers to native starch and to starch derivatives having an average polymerization degree of more than 10 glucose units. The starch used may be of various origin, such as potato starch, corn starch, wheat starch, tapioca starch, pea starch, waxy-corn starch and high-amylose starch. Modified starch, obtained by chemical, enzymatic and/or physical modification of native starch, may also be used. The term starch as used herein also comprises such modified starch products.

The process according to the invention is carried out in aqueous medium. The starch solution to be used is obtained by heating an aqueous starch suspension above the gelatinizing temperature of the starch or by dissolving pre-gelatinized starch in water. The starch concentration in the reagent is preferably between 0.1 and 50 wt.%.

The process according to the invention is carried out at pH-values of between 6.0 and 8.3 and preferably between 7 and 8. The pH optimum is remarkably high, namely at approximately 7.5. This is surprising, because the pH-optimum of sucrose phosphorylase is at 7 and the pH-optimum of potato phosphorylase at 6.5. In order to keep the pH of the reagent at the desired value, preferably, a buffer is used, for instance bis-tris-propane (BTP).

Glucosyl fluoride serves as a glycosyl donor. G-1-F bears structural resemblance to G-1-P, but has as an advantage that the fluoride released during the reaction does not inhibit the desired conversion, because reversal is not possible.

Potato phosphorylase (PP; EC 2.4.1.1 ) occurs in potatoes and can be isolated therefrom according to conventional methods. Sucrose phosphorylase (SP; EC 2.4.1.7) occurs in specific microorganisms, such as *Leuconostoc mesenteroides*, and can also be isolated therefrom according to conventional methods. The enzymes can be used in different forms, for instance as purified composition or in immobilized form. As inorganic phosphate (Pi) various soluble phosphate salts are suitable, like orthophosphate.

The reaction temperature to be used is preferably between 0° and 50° C. and in particular between 30° and 40° C., Above 50° C. the spontaneous hydrolysis of G-1-F increases strongly, so that the reaction efficiency decreases. The reaction time is not limited but is preferably between 1 and 101) hours.

The invention will be explained on the basis of the following examples.

Example 1 (Comparative Example)

Reaction mixtures with a volume of 3 milliliters wherein 25 mM α-glucose-1-fluoride, 0.25% dissolved starch, 200 mM bis-tris-propane as a buffer and an amount of potato phosphorylase (0.2 units per milliliter (u/ml)) are present, were incubated for 21 hours at 35° C. and at pH-values of respectively 7, 8 and 9. The conversion of the α-glucose-1-fluoride was determined by the measuring amount of fluoride formed, with an ion-selective electrode (Orion 96-09). After incubation, approximately 25% was converted. This was as much as in a mixture of the same composition as described above wherein no enzyme was present. Analysis by means of thin-layer chromatography on silica gel 60 showed that in the reaction mixture, only glucose was formed. No polymerization had taken place in the mixtures. No precipitates were visible in the reaction mixtures and, as far as optical density is concerned, with an iodine coloring of the starch at 550 nm no difference from the mixtures without enzyme could be seen. Moreover, during thin-layer chromatography, it appeared that the polymer spot was not more intense than that of the mixture without enzyme. Hence, starch polymerization by means of potato phosphorylase with the use of α-glucose-1-fluoride as glucosyl donor is not possible.

Example 2 (Comparative Example)

In the same manner as described in Example 1 an experiment was conducted, wherein instead of G-glucose-1-fluoride, α-glucose-1-phosphate was included in the reaction mixture.

In the reaction mixtures with α-glucose-1-phosphate, polymerization did take place. In the reaction mixtures with pH=7 and pH=8, a white precipitate was formed during the incubation. This precipitate could be colored blue by means of iodine. In the mixture with pH=9, no precipitate was formed during incubation. With iodine, this reaction mixture showed a higher optical density at 550 nm than the starting material. Analysis by means of thin-layer chromatography showed that the polymer spots were more intense than those in the mixtures without enzyme.

Example 3

Reaction mixtures with a volume of 3 milliliters containing 25 mM α-glucose-1-fluoride, 50 mM inorganic phosphate, 0.25% dissolved starch, 200 mM bis-tris-propane, sucrose phosphorylase (0.3 u/ml) and potato phosphorylase (0.2 u/ml) were incubated for 21 hours at 35° C. and pH-values of respectively 7, 7.5 and 8. After incubation, it appeared that more than 85% of the α-glucose-1-fluoride was converted. No precipitate could be seen in the reaction mixtures, but iodine coloration showed a clear (mixtures with pH=7 and pH=7.5) or a slight (pH=8) increase of the optical density at 550 nm compared to the mixtures without enzyme. This indicates that chain extension has indeed taken place.

Example 4

Reaction mixtures with a volume of 3 milliliters containing 100 mM α-glucose-1-fluoride, 100 mM inorganic phosphate, 0.25% dissolved starch, 200 mM bis-tris-propane, 0.3 u/ml sucrose phosphorylase and 0.2 u/ml potato phosphorylase were incubated for 21 hours at 35° C. and a pH of 6.5, 7.5, or 8.5. After incubation, 85% of the α-glucose-1-fluoride was converted in the mixtures with pH=6.5 and pH=7.5. A precipitate was formed in these reaction mixtures. Analysis by means of thin-layer chromatography indicated that α-glucose-1-phosphate was present in the reaction mixture. In the mixture with pH=8.5, only 32.2% of the α-glucose-1-fluoride was converted. No precipitate was formed in the reaction mixture. Thin-layer chromatography showed that only a slight amount of α-glucose-1-phosphate was present in the reaction mixture.

The precipitate and possibly dissolved polymeric carbohydrate were isolated from the reaction mixtures by means of ethanol precipitation (75 vol.%). After centrifugation, the pellets were successively washed with 75 vol.% and 100% ethanol. The pellets were suspended once again in the original volume of demineralized water.

The precipitate in the reaction mixtures proved to consist of carbohydrate. The yield of polymeric material in the mixture with pH=6.5 was 3.6 mg/ml, in the mixture with pH=7.5, this was 7.6 mg/ml and in the mixture with pH=8.5, 2.6 mg/ml.

The average chain length of the polymeric product formed at pH=6.5 was 40 glucose units, of the product formed at pH=7.5 45 glucose units and of the product at pH=8.5 14 glucose units. The degrees of branching were respectively 1.4% 0.5% and 1.7% The average chain length of the dissolved starch is 22 glucose units with a degree of branching of 3.0%.

At pH=6.5 and at pH=7.5 in a mixture with α-glucose-1-fluoride, phosphate, dissolved starch, sucrose phosphorylase and potato phosphorylase, chain extension of starch takes place. On the other hand, at pH=8.5 no chain extension takes place. The efficiencies are: at pH=6.5, 6.0% of the α-glucose-1-fluoride is converted into polymeric material and 21.8% into α-glucose-1-phosphate. At pH=7.5 28.0% is converted into polymeric material and 29.1% into α-glucose-1-phosphate. Hence, the efficiency is highest at pH=7.5. This pH is higher than the pH-optima of both enzymes. These pH-optima are respectively pH=7 for sucrose phosphorylase and pH=6.5 for potato phosphorylase.

We claim:

1. A process for polymerizing starch to provide chain-extended starch comprising reacting starch in an aqueous solution at a concentration of between 0.1 and 50 wt. % with glucosyl fluoride, said reaction being conducted at a pH of 6.0–8.3 and in the presence of a catalyst system, said catalyst system comprising inorganic phosphate, sucrose phosphorylase and potato phosphorylase.

2. The process of claim 1 wherein said pH is 7.0–8.0.

3. The process of claim 1 wherein said polymerization is carried out at a reaction temperature of up to 50° C.

4. The process of claim 3 wherein said temperature is from about 30° C. to about 40° C.

* * * * *